US010195607B2

(12) United States Patent
Asogawa et al.

(10) Patent No.: US 10,195,607 B2
(45) Date of Patent: Feb. 5, 2019

(54) MICROCHIP, DNA ANALYSIS METHOD AND DNA ANALYSIS SYSTEM

(71) Applicant: NEC Corporation, Tokyo (JP)

(72) Inventors: Minoru Asogawa, Tokyo (JP); Hisashi Hagiwara, Tokyo (JP); Yoshinori Mishina, Tokyo (JP); Yasuo Iimura, Tokyo (JP)

(73) Assignee: NEC Corporation, Tokyo (JP)

( * ) Notice: Subject to any disclaimer, the term of this patent is extended or adjusted under 35 U.S.C. 154(b) by 350 days.

(21) Appl. No.: 14/778,260

(22) PCT Filed: Mar. 6, 2014

(86) PCT No.: PCT/JP2014/055721
§ 371 (c)(1),
(2) Date: Sep. 18, 2015

(87) PCT Pub. No.: WO2014/148265
PCT Pub. Date: Sep. 25, 2014

(65) Prior Publication Data
US 2016/0288119 A1 Oct. 6, 2016

(30) Foreign Application Priority Data
Mar. 21, 2013 (JP) ................................ 2013-059106

(51) Int. Cl.
| | | |
|---|---|---|
| *C12Q 1/68* | (2018.01) | |
| *C12P 19/34* | (2006.01) | |
| *B01L 3/00* | (2006.01) | |
| *B01L 7/00* | (2006.01) | |
| *C12Q 1/6837* | (2018.01) | |
| *C12Q 1/686* | (2018.01) | |
| *G01N 27/447* | (2006.01) | |

(52) U.S. Cl.
CPC ..... *B01L 3/50273* (2013.01); *B01L 3/502753* (2013.01); *B01L 7/52* (2013.01); *C12Q 1/686* (2013.01); *C12Q 1/6837* (2013.01); *B01L 2200/10* (2013.01); *B01L 2300/0627* (2013.01); *B01L 2300/0816* (2013.01); *B01L 2300/0838* (2013.01); *B01L 2300/0867* (2013.01); *B01L 2300/0887* (2013.01); *B01L 2300/1822* (2013.01); *B01L 2300/1827* (2013.01); *B01L 2400/0421* (2013.01); *B01L 2400/0487* (2013.01); *C12Q 2531/113* (2013.01); *G01N 27/44791* (2013.01)

(58) Field of Classification Search
None
See application file for complete search history.

(56) References Cited

U.S. PATENT DOCUMENTS

| | | | |
|---|---|---|---|
| 6,554,985 B2 | 4/2003 | Ruiz-Martinez et al. | |
| 7,588,671 B2 | 9/2009 | Morita et al. | |
| 8,202,722 B2 | 6/2012 | Asogawa et al. | |
| 8,470,266 B2 | 6/2013 | Asogawa et al. | |
| 8,623,294 B2 | 1/2014 | Asogawa et al. | |
| 8,741,231 B2 | 6/2014 | Asogawa et al. | |
| 8,845,980 B2 | 9/2014 | Asogawa et al. | |
| 9,186,671 B2* | 11/2015 | Augstein | B01L 3/502723 |
| 2002/0009721 A1 | 1/2002 | Ruiz-Martinez et al. | |
| 2002/0068357 A1 | 6/2002 | Mathies et al. | |
| 2005/0161326 A1 | 7/2005 | Morita et al. | |
| 2009/0294287 A1 | 12/2009 | Morita et al. | |
| 2010/0112681 A1 | 5/2010 | Asogawa et al. | |
| 2010/0323432 A1 | 12/2010 | Asogawa et al. | |
| 2011/0000561 A1 | 1/2011 | Asogawa et al. | |
| 2011/0002812 A1 | 1/2011 | Asogawa et al. | |
| 2012/0055798 A1 | 3/2012 | Selden et al. | |
| 2012/0230888 A1 | 9/2012 | Asogawa et al. | |
| 2013/0251603 A1 | 9/2013 | Asogawa et al. | |
| 2014/0079605 A1 | 3/2014 | Asogawa et al. | |

FOREIGN PATENT DOCUMENTS

| | | |
|---|---|---|
| JP | 7-322881 | 12/1995 |
| JP | 2002-529734 | 9/2002 |
| WO | WO 2005/049196 A1 | 6/2005 |
| WO | WO 2008/108481 A1 | 9/2008 |
| WO | WO 2009/035061 A1 | 3/2009 |
| WO | WO 2009/035062 A1 | 3/2009 |
| WO | WO 2009/038203 A1 | 3/2009 |
| WO | WO 2009/119698 A1 | 10/2009 |

OTHER PUBLICATIONS

Xie et al., "High resolution single strand conformation polymorphism analysis using formamide and ethidium bromide staining," Molecular Pathology, vol. 50, No. 5, pp. 276-278. (Year: 1997).*
M. Asogawa, "DNA o Mochiita Kojin Shikibetsu to sono Gijutsu", NEC Technical Journal, vol. 63, No. 3, pp. 31-34 [online], [retrieval date Jun. 2, 2014], Internet URL:http://jpn.nec.com/techrep/journal/g10/n03/pdf/100307.pdf, 2010.
H. Tian et al., Single-Strand Conformation Polymorphism Analysis by Capillary and Microchip Electrophoresis: A fast, Simple Method for Detection of Common Mutations in BRCA1 and BRCA2, Genomics 63, pp. 25-34, 2000.
International Search Report and Written Opinion dated Jun. 10, 2014 in corresponding PCT International Application.
D. Manage et al., "On-chip HA/SSCP for the detection of hereditary haemochromatosis", Microfluidics and Nanofluidics, Springer, vol. 1, No. 4, pp. 364,372, Jul. 2005.
G. Vahedi et al., "An integrated method for mutation detection using on-chip sample preparation, single-stranded conformation polymorphism, and heteroduplex analysis", Electrophoresis, vol. 25, No. 14, pp. 2346-2356, 2369, Abstract, Jul. 2004.

(Continued)

*Primary Examiner* — Young J Kim
(74) *Attorney, Agent, or Firm* — Finnegan, Henderson, Farabow, Garrett & Dunner, L.L.P.

(57) ABSTRACT

A microchip comprises a PCR section, a denaturing section, and an electrophoresis section. In the PCR section, a desired region in DNA is amplified. In the denaturing section, PCR amplicon of double-strand DNA is denatured into single-strand DNA. In the electrophoresis section, the PCR amplicon is separated based on the length of sequence.

5 Claims, 15 Drawing Sheets

(56) References Cited

OTHER PUBLICATIONS

M. Orita et al., "Rapid and Sensitive Detection of Point Mutations and DNA Polymorphisms Using the Polymerase Chain Reaction", Genomics, Academic Press, vol. 5, No. 4, pp. 874-879, Nov. 1989.
H. Tian et al., "Single-Strand Conformation Polymorphism Analysis by Capillary and Microchip Electrophoresis: A Fast, Simple Method for Detection of Common Mutations in BRCA1 and BRCA2", Genomics, Academic Press, vol. 63, No. 1, pp. 25-34, Jan. 2000.
P. Sunnucks et al., "SSCP is not so difficult: the application and utility of single-stranded conformation polymorphism in evolutionary biology and molecular ecology", Molecular Ecology, vol. 9, No. 11, pp. 1699-1710, Nov. 2000.
S. Shin et al., "Separation and Size Determination of Circular and Linear Single-Stranded DNAs by Alkaline Agarose Gel Electrophoresis[1]", Analytical Biochemistry, Academic Press, Inc., vol. 226, pp. 202-206, Apr. 1995.
Extended European Search Report dated Nov. 11, 2016, by the European Patent Office in counterpart European Patent Application No. 14769006.9.

\* cited by examiner

MICROCHIP, DNA ANALYSIS METHOD AND DNA ANALYSIS SYSTEM

CROSS-REFERENCE TO RELATED APPLICATION

The present Application is a National Stage Entry of International Application No. PCT/JP2014/055721, filed Mar. 6, 2014, which claims priority from Japanese Patent Application 2013-059106 filed Mar. 21, 2013, the entire contents thereof being incorporated by reference into the present application.

FIELD

This invention relates to a microchip, a DNA analysis method and a DNA analysis system, more particularly, to a microchip having reaction chambers interconnected with fine flow paths and the DNA analysis method and the DNA analysis system using the microchip thereof.

BACKGROUND

Electrophoresis is carried out for DNA (deoxyribonucleic acid), ions or low molecular compounds as targets for analysis. In particular, since individual identification with DNA is a useful means for efficiently narrowing down candidates in criminal investigation, there is an increasing need for electrophoresis for DNA as a target.

Patent Literatures (PTLs) 1 to 5 disclose microchips in which charging chambers and fine flow paths are arranged on a single chip. The microchips of Patent Literatures 1 to 5 have a multi-layered structure in which a plurality of plates are laminated, and sample chambers and reaction chambers are formed by perforations on a part of the plurality of plates. In addition, these sample chambers and reaction chambers are pressurized from outside to extrude the solution into the fine flow paths between the sample chambers and reaction chambers to control transfer of the solutions.

Furthermore, non Patent Literature (NPL) 1 discloses a DNA analysis apparatus that carries out process steps necessary for DNA analysis on a microchip.

PTL 1: International Application Publication No. WO2008/108481A
PTL 2: International Application Publication No. WO2009/035061A
PTL 3: International Application Publication No. WO2009/035062A
PTL 4: International Application Publication No. WO2009/038203A
PTL 5: International Application Publication No. WO2009/119698A
Non-Patent Literature 1: NEC Corporation, "Individual Identification with DNA and Technology thereof", September 2010, [online], [Retrieved on Jan. 23, 2013, Internet].

SUMMARY

The disclosures of the above mentioned related technical literatures are to be incorporated herein by reference. The following analysis is made by the present inventors.

There is a problem that the technologies disclosed in the above related art documents have a poor precision in analysis. That is, individual identification with DNA is used in criminal investigation, thus a high precision in analysis is required. However, the technologies disclosed in the related art documents detect a ghost peak, resulting in occurrence of insufficiency in the analysis precision required.

It is an object of the present invention to provide a microchip, a DNA analysis method and a DNA analysis system contributing to improved analysis precision of DNA.

In a first aspect of the present invention, there is provided a microchip comprising a PCR section in which a desired region in a template DNA is amplified; a denaturing section in which amplicon amplified in the PCR section is denatured from double-strand DNA into single-strand DNA; and an electrophoresis section in which the amplicon is separated based on the length of sequence.

In a second aspect of the present invention, there is provided a DNA analysis method in which, on a microchip, a desired region in a template DNA is amplified, the amplified amplicon is denatured from double-strand DNA into single-strand DNA, and the amplicon is separated based on the length of sequence.

In a third aspect of the present invention, there is provided a DNA analysis system comprising: a microchip comprising a PCR section in which a desired region in a template DNA is amplified; a denaturing section in which amplicon amplified in the PCR section is denatured from double-strand DNA into single-strand DNA; and an electrophoresis section in which the amplicon is separated based on the length of sequence, and a DNA analysis apparatus for executing DNA analysis by controlling PCR in the PCR section, denaturation in the denaturing section and electrophoresis in the electrophoresis section.

In these aspects of the present invention, there may be provided a microchip, a DNA analysis method and a DNA analysis system contributing to improving analysis precision of DNA.

PREFERRED MODES

Figure 1:
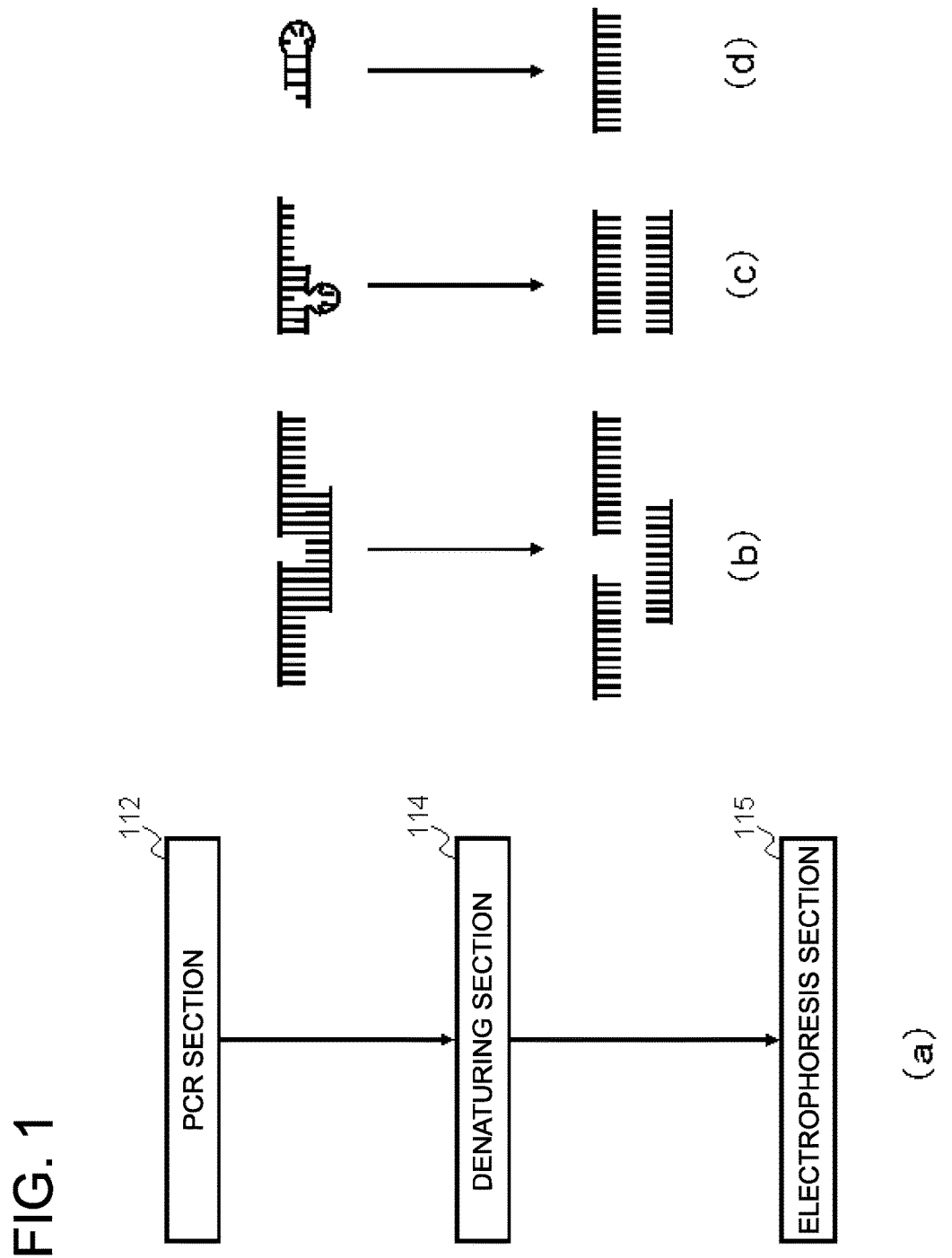
FIG. 1 is a schematic view for illustrating a summary of an exemplary embodiment.

In first, a mode of the present invention will now be summarized with reference to FIG. 1. It is noted that symbols in the summary are merely examples to assist in understanding and are not intended to limit the present invention to the mode shown in the summary.

An microchip according to an exemplary embodiment comprises a PCR section 112 in which a desired region in a template DNA is amplified; a denaturing section 114 in which the amplified amplicon is denatured from double-strand DNA into single-strand DNA; and an electrophoresis section 115 in which the amplicon is separated based on the length of sequence.

That is, as shown in FIG. 1, analysis precision is improved by executing the electrophoresis after DNA denaturation process so as to overcome generation of a ghost peak due to generation of a bridge structure (FIG. 1 (b)), a bulge loop structure (FIG. 1 (c)), and a hairpin structure (FIG. 1 (d)).

An exemplary embodiment will now be explained specifically.

Exemplary Embodiment 1

Exemplary Embodiment 1 will be explained in detail with reference to the drawings.

Figure 2:
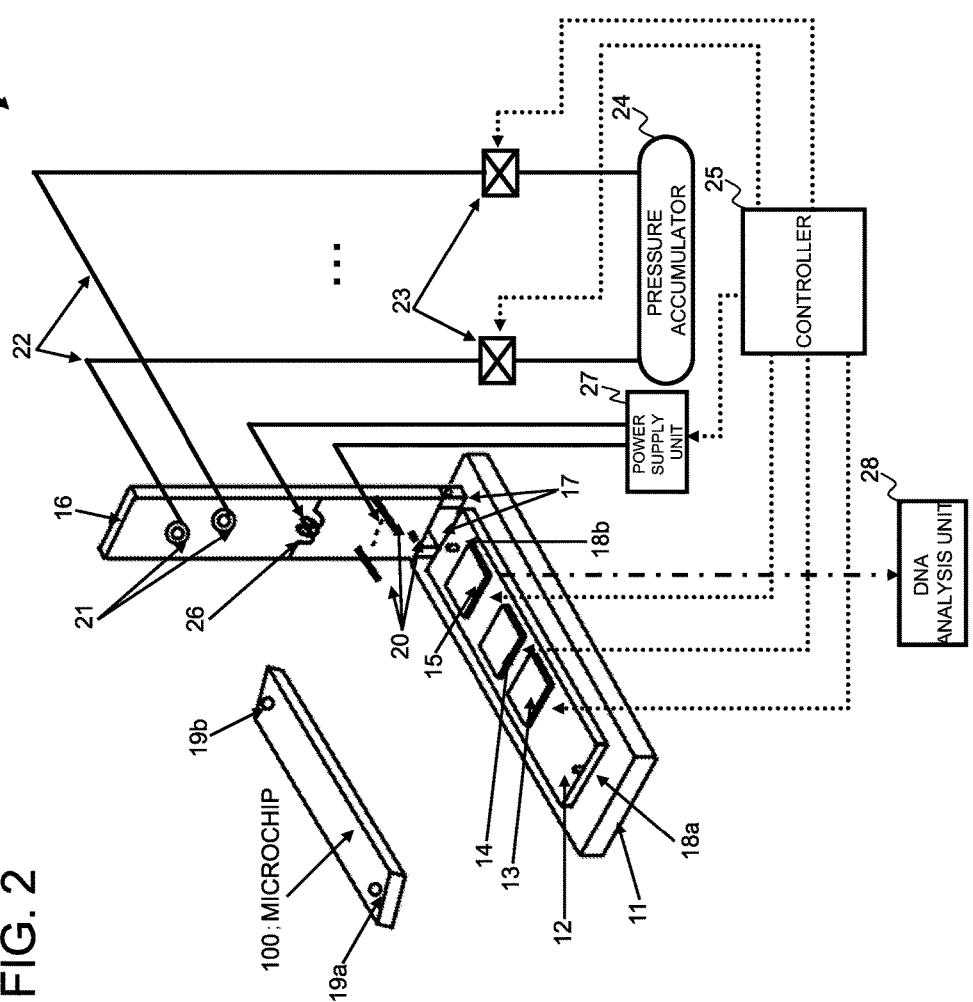
FIG. 2 is a perspective view showing a configuration of a DNA analysis apparatus 10 according to exemplary embodiment 1.

FIG. 2 depicts a perspective view showing a configuration of a DNA analysis apparatus 10 according to the subject exemplary embodiment.

Referring to FIG. 2, a table 12 is arranged on a base member 11. In the table 12, temperature adjustment units 13, 14 are embedded. The temperature adjustment unit 14 is also referred to as a temperature adjustment section. An electrophoresis unit 15 is arranged on the table 12. The base member 11 and a lid 16 are joined with a hinge 17 to allow opening/closure of the lid 16.

A microchip 100 used in the DNA analysis apparatus 10 according to the subject exemplary embodiment is of a multi-layer structure in which a plurality of plates are laminated, as disclosed in Patent Literature 5. Sample chambers and reaction chambers are formed by perforations on a part of the plurality of plates. The microchip 100, used for DNA analysis, is installed at a predetermined position in a manner where pins 18a, 18b provided on the table 12 are engaged with pin holes 19a, 19b provided on the microchip 100. If, in a state that the microchip 100 is arranged on the table 12, the lid 16 is closed, certain regions of the microchip 100 are brought into contact with the temperature adjustment units 13, 14. In addition, by closing the lid 16, certain regions of the microchip 100 are brought into contact with a surface of the electrophoresis unit 15, at the same time as electrodes 20 are introduced into electrode chambers, respectively, provided on the microchip 100.

A plurality of pressurizing holes 21 are provided on the lid 16. The pressurizing holes 21 are through-holes formed on the lid 16 and are connected to solenoid valves 23 via tubes 22. On closing the lid 16, the pressurizing holes 21, formed on the lid 16, are brought into contact with certain regions on the microchip 100.

A pressure accumulator 24 stores compressed air which may be released via the pressurizing holes 21 on the lid 16 by the controller 25 controlling the solenoid valves 23. The internal pressure within the pressure accumulator 24 is controlled by a pressure sensor, a pump etc., not shown, so as to be maintained at a predetermined value of pressure. By the way, the microchip 100 of the subject exemplary embodiment has a flow path opening/closing function disclosed e.g., in Patent Literature 5. The controller 25 controls the solenoid valve(s) 23 to apply pressure on a part of the microchip 100 via the pressurizing holes 21 formed on the lid 16. This extrudes the solution from a reaction chamber to a flow path provided on the microchip 100 so as to transfer the solution to an objective reaction chamber. For example, in a case where the solution is to be transferred from a reaction chamber A into a reaction chamber B, part of a flow path ahead of the reaction chamber B is pressured, while a flow path between the reaction chambers A, B is not. If the reaction chamber A is pressured under such state, the solution, accumulated in the reaction chamber A, is extruded into a flow path communicating the reaction chambers A and B. Since the flow path ahead of the reaction chamber B is pressured, the solution extruded is caused remains in the reaction chamber B. Transfer of the solution between the reaction chambers is achieved in such manner.

Moreover, an electromagnet coil 26 is arranged on the lid 16 and supplied with power from a power supply unit 27 so that a magnetic field may be generated in a predetermined region on the microchip 100. It is noted that the controller 25 instructs the power supply unit 27 to supply and to stop the supply of the electrical power to the electromagnet 26 so as to regulate excitation of the electromagnet 26.

The temperature adjustment units 13, 14 control the temperature of a predetermined region (or regions) on the microchip 100. The temperature adjustment units 13, 14 will be explained in detail below.

The electrodes 20 and the electrophoresis unit 15 are used in carrying out electrophoresis on the microchip 100. In more detail, in the process of the electrophoresis for the microchip 100, the controller 25 applies a dc voltage to the electrodes 20 via the power supply unit 27. When the dc voltage is applied to the electrodes 20, a charged DNA fragment migrates through the inside of the capillary. The electrophoresis unit 15 comprises a means for irradiating laser light and a means for receiving fluorescence emitted by excitation with the laser light irradiation. An output of the laser light receiving means, installed in the electrophoresis unit 15, is sent to a DNA analysis unit 28 so as to be used for analysis (determination) of the DNA length. By the way, the electrophoresis unit 15 will be explained in detail below.

Figure 3:
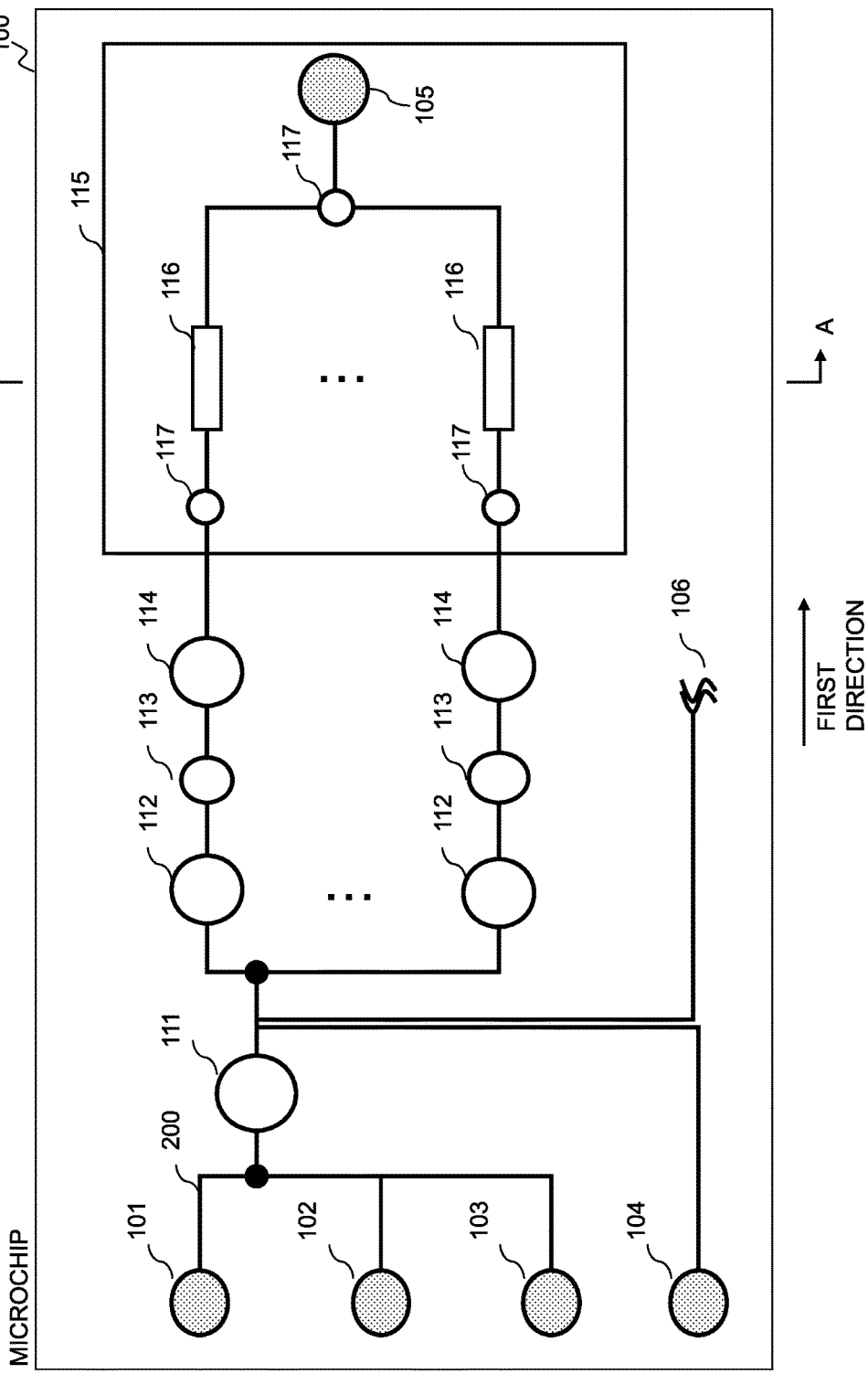
FIG. 3 is a view showing an exemplary configuration of a microchip 100.

The configuration of the microchip 100 will now be explained. FIG. 3 depicts an exemplary configuration of the microchip 100.

[Configuration of a Microchip]

Referring to FIG. 3, the microchip 100 comprises a sample solution injection section 101, a wash buffer injection section 102, a PCR reagent injection section 103, a formamide injection section 104, an electrophoresis polymer injection section 105, a drainage port 106, a DNA extraction section 111, a PCR section 112, a volume determination section 113, a denaturing section 114, an electrophoresis section 115, a set of capillaries 116 and a flow paths 200 communicating the above sections etc.

Figure 4:
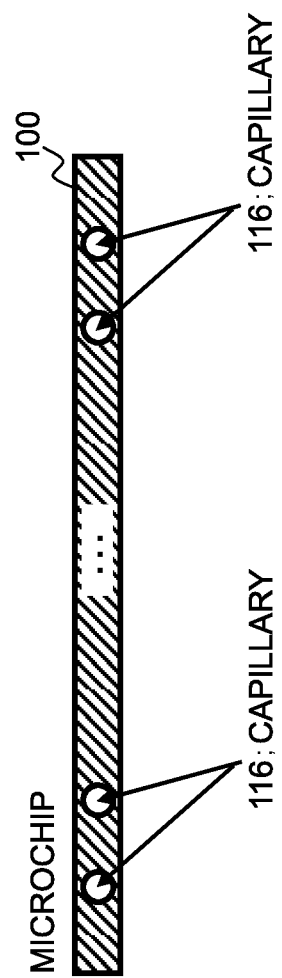
FIG. 4 is an exemplary cross-sectional view taken along line A-A of FIG. 3.

Each capillary 116 is provided inside of the microchip 100 and may be extended in a first direction shown in FIG. 3. FIG. 4 shows an exemplary cross-section taken along line A-A of FIG. 3. A plurality of capillaries 116 are extended inside of the microchip 100. The microchip 100 is planar in shape and has a thickness smaller than its width or depth. The electrophoresis section 115 comprises a set of electrode chambers 117 into which a set of electrodes 20 arranged on the lid 16 is introduced at the time of DNA analysis. The set of electrode chambers 117 comprises an electrode chamber into which an anode (positive electrode) is introduced and an electrode chamber into which a cathode (negative electrode) is introduced. Both of these two types of the electrode chambers are connected to the capillaries 116.

The sample solution injection section 101 has a recessed structure into which a user injects a sample solution. The sample solution is a solution in which cells taken from a person, such as mouth mucosa, blood or body fluid, are suspended in a lysis buffer, such as SDS/LiOAc solution (sodium dodecyl sulfate/lithium acetate solution).

The wash buffer injection section 102 also has a recessed structure into which a wash buffer is injected by the user. The wash buffer is e.g., a Tris buffer and being prepared at a high salt concentration to maintain binding of DNA to silica.

The PCR reagent injection section 103 also has a recessed structure into which a PCR reagent solution is injected by the user. A PCR reagent contains polymerase, dNTPs, magnesium and so forth and plays a role as an elution buffer for eluting DNA from silica. Hence, the PCR reagent is prepared at a low salt concentration.

The formamide injection section 104 also has a recessed structure and a formamide solution is injected by a user into this formamide injection section. A formamide solution is a reagent that keeps the DNA in a single-strand state. That is, repeated under denaturing process are denaturalization, also referred to as dissolving or separation, in which DNA is denatured from the double-strand state to the single-strand state and hybridization, also referred to as annealing or binding, in which DNA is converted from the single-strand state into the double-strand state. It should be noted that, formamide keeps DNA in the single-strand state, resulting in that formamide acts to denature the double-strand DNA to the single-strand DNA. As above, in the present Application, the terms 'keep' and 'denaturing' are sometimes used interchangeably. The formamide solution also contains an ssDNA (single-strand DNA) size marker labeled with a fluorescent dye.

The electrophoresis polymer injection section 105 also has a recessed structure, into which a polymer for electrophoresis is injected by the user.

By the way, the lysis buffer, wash buffer, PCR reagent, formamide, ssDNA size marker as well as the polymer are commercially available. These reagents may also be prepared in a different composition. The wash buffer, PCR reagent, formamide solution as well as the polymer may be pre-sealed in the microchip 100 instead of being injected by the user.

The DNA extraction section 111 is a reaction chamber to extract DNA from the sample solution. In the following description, the DNA extracted from the sample solution is also referred to as a template DNA.

The processing of extracting DNA will now be explained in detail. The DNA analysis apparatus 10 comprises an electromagnet 26 facing the DNA extraction section 111. In this DNA extraction section 111, silica-coated magnetic beads are pre-sealed. In the DNA analysis apparatus 10, the sample solution injected into the sample solution injection section 101 is transferred to the DNA extraction section 111 where the sample DNA is adsorbed to the magnetic beads (silica) sealed in the DNA extraction section 111. The magnetic beads are rinsed with the wash buffer in the wash buffer injection section 102 to extract the template DNA. It should be noted that, when the DNA analysis apparatus 10 discharges the sample solution and the wash buffer via the drainage port 106, the magnetic beads are absorbed by the electromagnet 26 to prevent the magnetic beads from being discharged along with the sample solution and the wash buffer.

By the way, as a method for DNA extraction with the magnetic beads, it is known to use a MagExtractor (registered trademark) manufactured by TOYOBO CO. LTD and NucleoMag (registered trademark) manufactured by TAKARA-BIO CO. LTD. The protocol for DNA extraction may be modified as necessary such as by increasing the number of times of rinsing. The method for DNA extraction is not limited to using the magnetic beads. A silica beads column, for example, may be used to extract the template DNA. See for example QIAamp of Qiagen Co. Ltd.

The PCR section 112 is one or more reaction chambers provided halfway in order to carry out PCR which amplifies a desired segment of the template DNA. Each PCR section 112 is provided adjacent to the temperature adjustment unit 13. In each PCR section 112, there is sealed a primer set designed to amplify a desired segment of the template DNA.

The primer set is a forward primer and a reverse primer for PCR amplification of a segment comprising a microsatellite, such as TPOX or FGA. One or both of the primers are labeled with fluorescent dye, such as fluorescein. Such primer is commercially available from Promega Corporation (Promega, a registered trademark), and may also be designed as necessary. A plurality of primer sets may be sealed in one PCR section 112.

Figure 5:
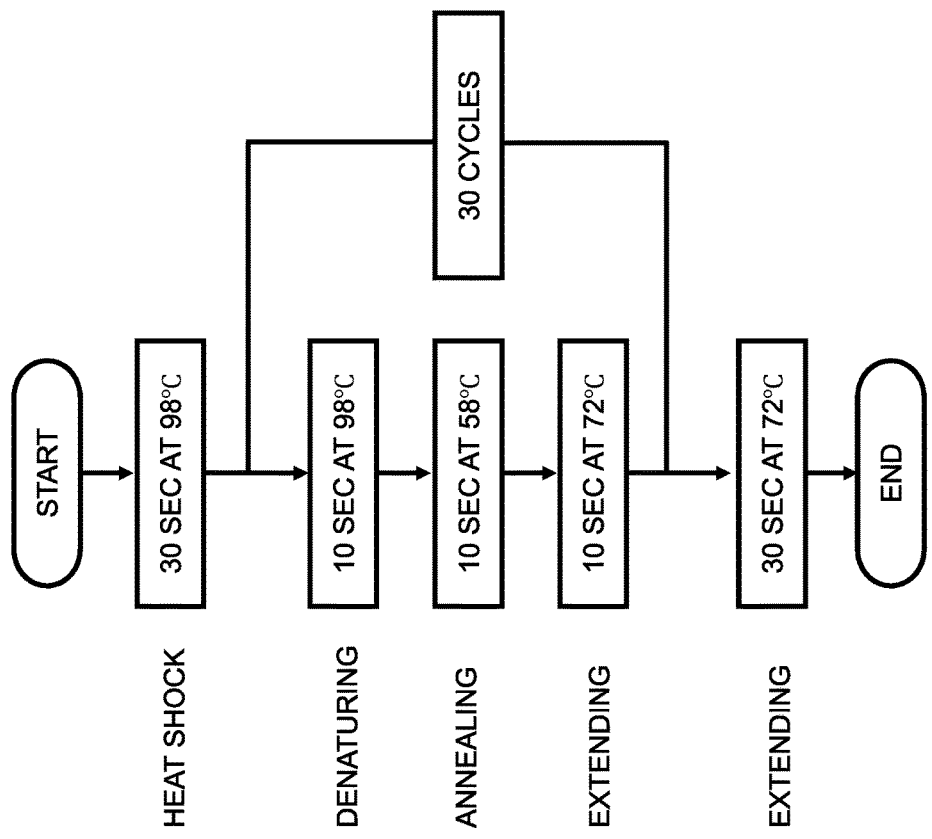
FIG. 5 is a flowchart showing an exemplary PCR program.

The PCR (the polymerase chain reaction) will now be specifically explained. In the DNA analysis apparatus 10, a PCR reagent containing a template DNA is transferred from the DNA extraction section 111 to a plurality of the PCR sections 112. The temperature of the PCR sections 112 is controlled in a programmed manner by a heat conductive material of the temperature adjustment unit 13. In an example PCR programming, the DNA analysis apparatus 10 executes PCR by temperature control in accordance with temperature and time setting shown in FIG. 5. The temperature conditions of the PCR as well as the number of cycles may be modified based on the Tm (melting temperature) value or the length of the amplicon. The DNA, amplified by PCR, is referred to as 'amplicon' and a PCR reagent containing the amplicon is referred to as a reaction sample hereinafter.

The volume determination section 113 is a reaction chamber for disposing a part of the reaction sample, particularly having a smaller capacity than the PCR section 112. The volume determination processing will now be explained. The DNA analysis apparatus 10 transfers the reaction sample from the PCR section 112 to the volume determination section 113 until the volume determination section is filled up, while discharging the remaining reagent via the drainage port 106.

The denaturing section 114 is a reaction chamber for denaturing the amplicon from the double strand DNA (dsDNA) to the single stand DNA (ssDNA), and is arranged adjacent to the temperature adjustment unit 14. The denaturing processing will now be explained in detail. The temperature of the denaturing section 114 is kept by the DNA analysis apparatus 10 at a preset temperature, such as 60° C., via the temperature adjustment unit 14. The DNA analysis apparatus 10 transfers formamide injected into the formamide injection section 104 to the denaturing section 114 via the PCR section 112 and the volume determination section 113. Since the amplicon amplified in the PCR section 112 flows into the denaturing section 114 together with the keeping reagent (formamide), the amplicon and the keeping reagent may be mixed together more hardly when compared with a case where the amplicon and the keeping reagent are allowed to flow independently into the denaturing section 114. The DNA analysis apparatus 10 operates to hold the reaction sample in the denaturing section 114 for a preset reaction time.

The electrophoresis section 115 is configured to separate the amplicon in accordance with the length of nucleic acid sequence by the molecular sieve effect, and is arranged so as to be adjacent to the PTC heater which will be explained below. More specifically, the electrophoresis section 115 comprises the capillaries 116 and is arranged adjacent to the PTC heater so as to maintain the capillaries 116 at an even temperature.

The processing of electrophoresis will be explained in more detail. The polymer in the electrophoresis polymer injection section 105 is charged into the capillaries 116 by the DNA analysis apparatus 10. The electrophoresis section 115 is maintained by the PTC heater at a preset temperature, such as at 50° C. The DNA analysis apparatus 10 transfers the reaction sample from the denaturing section 114 to the electrophoresis section 115 to inject the reaction sample into each of the capillaries 116. As an injection method, a so-called cross-injection method may be used (see for example JP Patent Publication No. 2002-310858A). When starting peak detection by a light receiving means, the DNA analysis apparatus 10 applies a dc voltage via the electrode chambers 117 connected to the capillaries 116.

The temperature adjustment units 13, 14 will now be explained.

The temperature adjustment unit 13 is a means for controlling temperature of the PCR section 112 on the microchip 100 under instructions from the controller 25.

Figure 6:
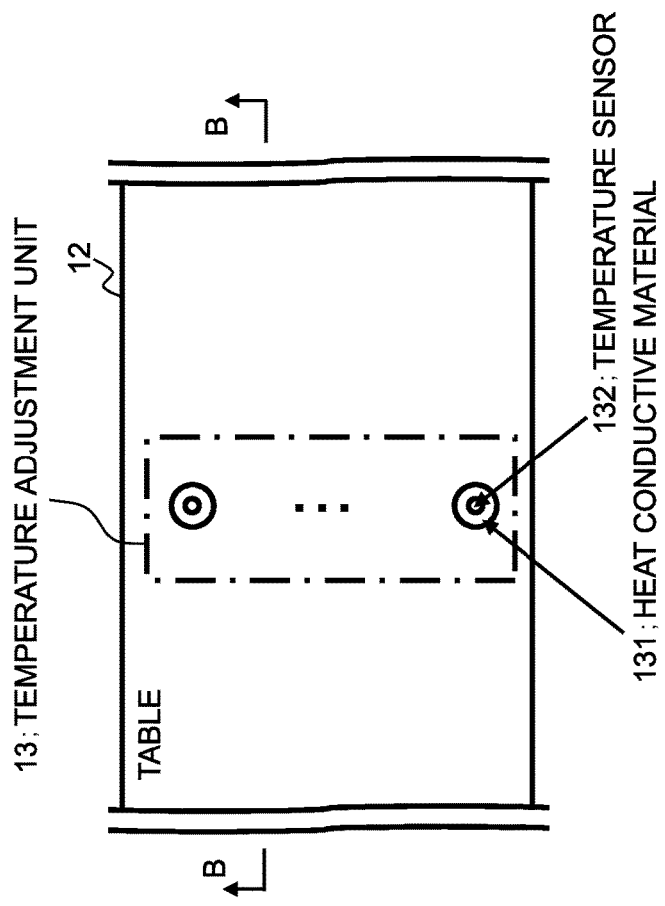
FIG. 6 is an exemplary plan view showing a region of a table 12 inclusive of a temperature adjustment unit 13.
Figure 7:
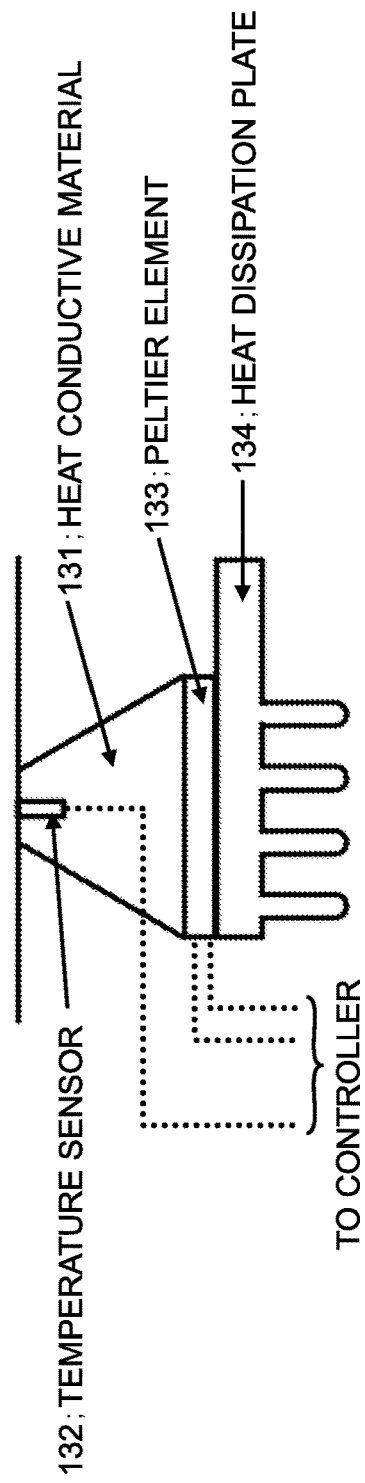
FIG. 7 is an exemplary cross-sectional view taken along line B-B of FIG. 6.

FIG. 6 depicts an exemplary plan view showing a certain region of the table 12 comprising the temperature adjustment unit 13. FIG. 7 depicts an exemplary cross-sectional view taken along line B-B of FIG. 6.

The temperature adjustment unit 13 is arranged in a certain region of the table 12 in an embedded manner, as stated above. Referring to FIG. 6, a heat conductive material 131 is exposed on a surface of the table 12, and a temperature sensor 132 is arranged at the center of the heat conductive material 131.

Referring to FIG. 7, the temperature sensor 132 is connected to the controller 25. The heat conductive material 131 has its one surface in contact with a temperature sensing (temperature applying) surface of a Peltier element 133. The Peltier element 133 has its temperature dissipation surface in contact with a surface of a heat dissipation plate 134. A power supply line of the Peltier element 133 is connected to the controller 25. The controller 25 acquires the temperature of the PCR section 112 from the temperature sensor 132 and, based on the so acquired temperature, decides the direction of the current delivered to the Peltier element 133 to control the heating or cooling of the Peltier element 133 to manage temperature control of the PCR section 112.

Figure 8:
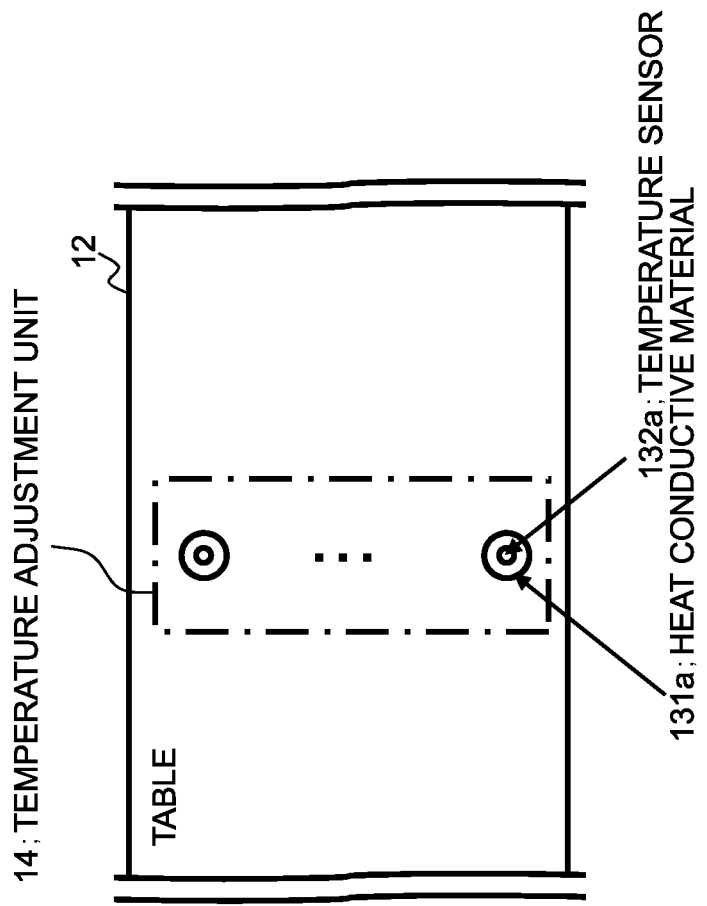
FIG. 8 is an exemplary plan view showing a region of the table 12 inclusive of a temperature adjustment unit 14.

The temperature adjustment unit 14 is a means for maintaining an even temperature of the denaturing section 114 on the microchip 100 based on an instruction from the controller 25. FIG. 8 depicts an exemplary plan view showing a region of the table 12 including the temperature adjustment unit 14. The temperature adjustment unit 14 may have the same configuration as the temperature adjustment unit 13, as shown in FIG. 8. It is however not intended to limit the structure of the temperature adjustment unit 14, such that it is possible to construct the temperature adjustment unit 14 using a heater, as an example.

The electrophoresis unit 15 will now be explained.

Figure 9:
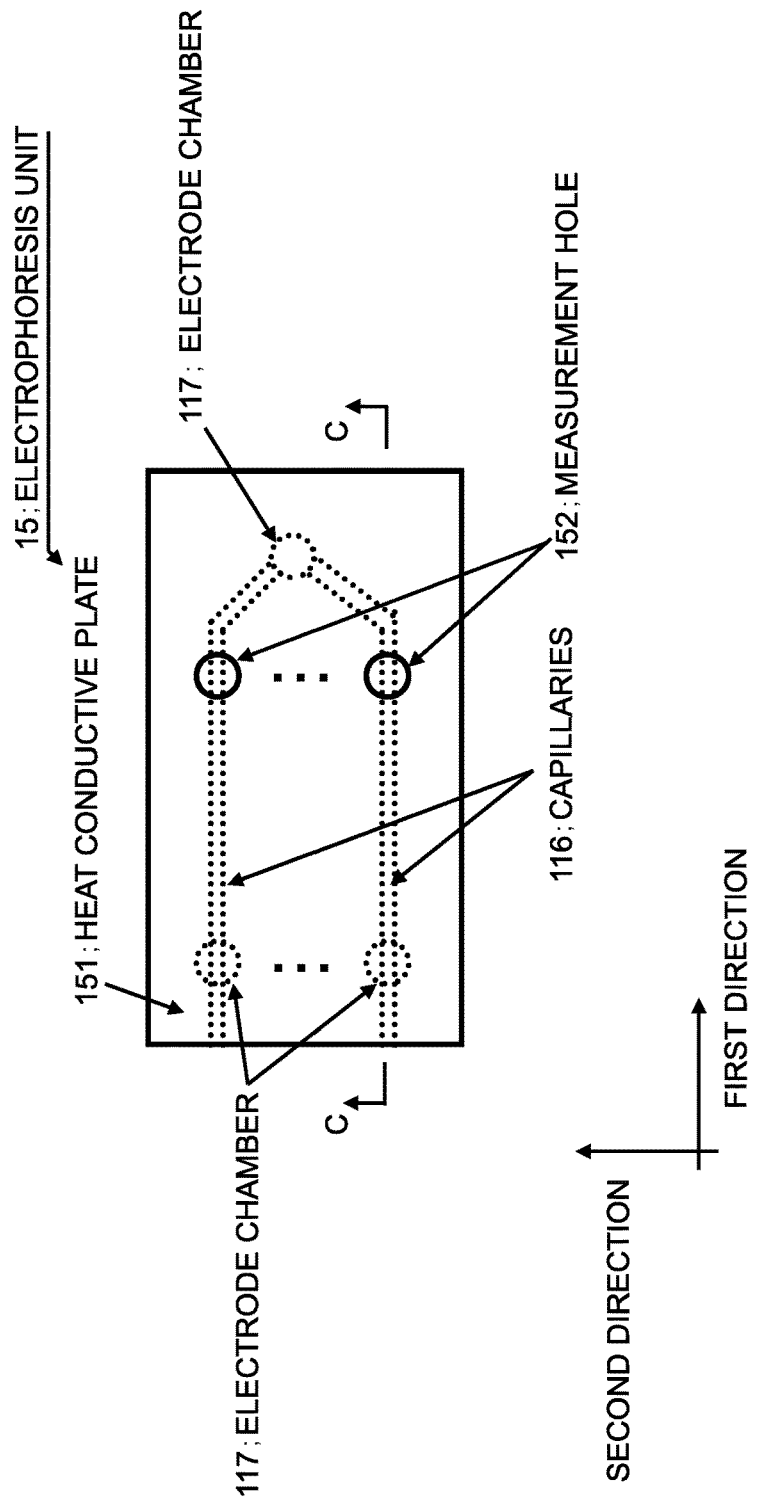
FIG. 9 is an exemplary plan view showing a region of the table 12 inclusive of an electrophoresis unit 15.
Figure 10:
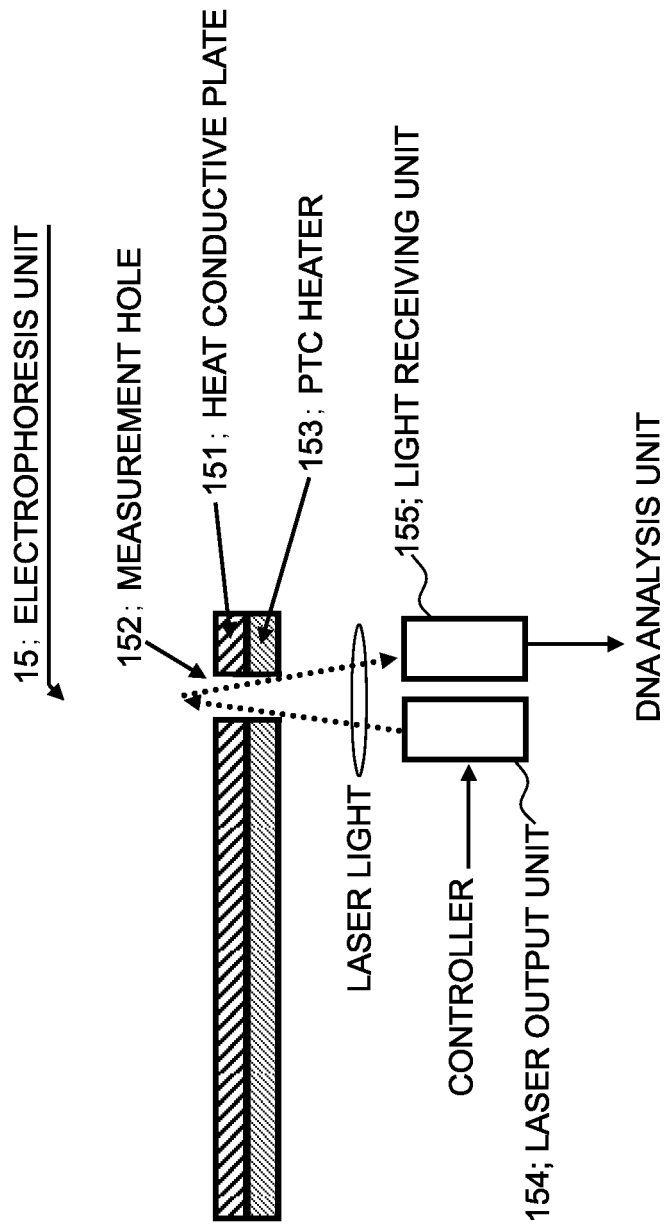
FIG. 10 is an exemplary cross-sectional view taken along line C-C of FIG. 9.

FIG. 9 depicts an exemplary plan view showing a region of the table 12 comprising the electrophoresis unit 15. FIG. 10 depicts an exemplary cross-sectional view taken along line C-C of FIG. 9. It is noted that the capillaries 116, shown by dotted line in FIG. 9, are provided not in the electrophoresis unit 15 but inside of the microchip 100. The set of electrode chambers 117, which are shown by dotted circles in FIG. 9, and into which the electrodes 20 are introduced, are also provided in the microchip 100. These components are only shown to assist in understanding in FIG. 9

Referring to FIG. 9, the electrophoresis unit 15 comprises a heat conductive plate 151, a through-hole 152 for passage of laser light used for measuring the DNA length is arranged thereon. Referring to FIG. 10, a PTC (positive temperature coefficient) heater 153 is arranged on the bottom surface of the heat conductive plate 151 in a laminated manner on the heat conductive plate 151. The measurement hole 152 is also provided on the PTC heater 153.

A laser output unit 154 comprises a laser diode that emits laser light towards the measurement hole 152. On/off of the irradiation of the laser light by the laser output unit 154 is controlled in accordance with instructions from the controller 25. A light receiving unit 155 receives fluorescence emitted from the DNA fragments passing through a site corresponding to the measurement hole 152 provided on the electrophoresis section 115. The light receiving unit 155 comprises a photomultiplier, as an example. The light receiving unit 155 converts the light reflected by a DNA, which has migrated by electrophoresis through the capillaries to a site directly above the measurement hole 152, into an electrical signal, which is output to the DNA analysis unit 28. Or, the light receiving unit 155 may comprise an image pickup element, such as a charge-coupled device (CCD), measuring the intensity of the reflected light, so as to detect the passage of the DNA through a site directly above the measurement hole 152.

It should be noted that the electrophoresis unit 15 radiates the laser light from below the microchip 100, that is, in a direction proceeding from the table 12 of FIG. 2 towards the lid 16. However, laser light radiation from the electrophoresis unit 15 is not limited to radiation from below the microchip 100. If, for example, the electrophoresis unit 15 is attached on the lid 16, the laser light is radiated from above the microchip 100. In this case, there is no necessity of providing the measurement hole 152 on the heat conductive plate 151.

Figure 11:
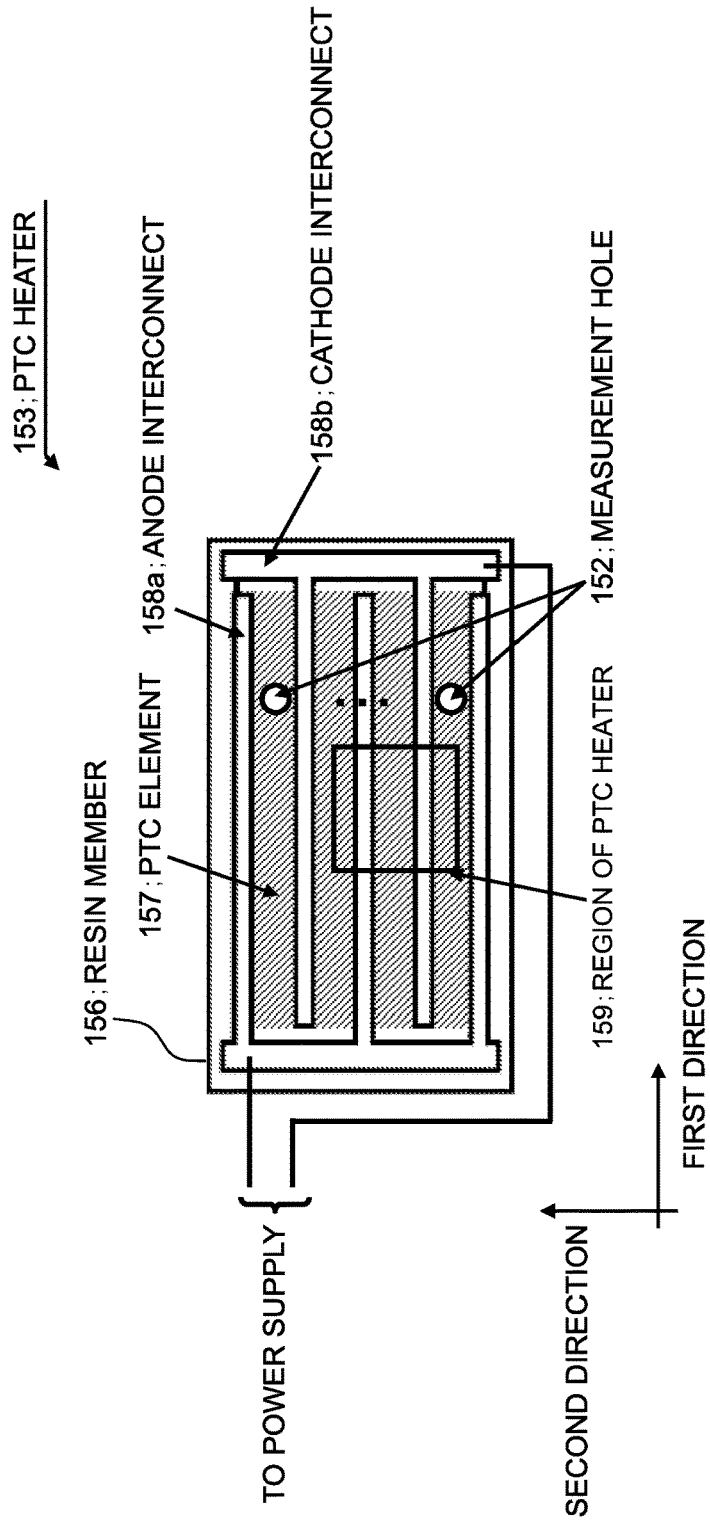
FIG. 11 is an exemplary plan view of a PTC heater 153.

FIG. 11 depicts an exemplary plan view of the PTC heater 153. The PTC heater 153 is a membrane heater comprising a PTC element 157, an anode interconnect 158*a* and a cathode interconnect 158*b* on a resin member 156 having the same shape as the heat conductive plate 151. The PTC heater 153 is arranged for supplying heat to the capillaries 116 and maintaining the capillaries 116 at an even temperature. The resin member 156 is of a size to fit to the electrophoresis section 115 of the microchip 100, thus of a size substantially equal to the electrophoresis section 115. The PTC element 157 as well as the electrode interconnects 158*a*, 158*b* are arranged on a surface of the resin member 156 which is in contact with the heat conductive plate 151. On applying a dc voltage across the electrode interconnects 158*a*, 158*b*, current flows through the PTC element 157. When the current flows through the PTC element 157, heat is generated by the PTC element 157 and supplied via the heat conductive plate 151 to the capillaries 116.

It should be noted that the PTC element 157 has a feature that, in case current flows through it so that it has reached a preset temperature, its electrical resistance decreases acutely. That is, the PTC element 157 acts as a current limiting element having a feature that when the current flows through the PTC element 157, its electrical resistance increases by self-heat generation to render current conduction difficult. If the current flowing through the PTC element 157 is decreased, power usage by the PTC element 157 is also decreased, resulting in that the temperature due to heat generation is lowered. The PTC heater 153, with the PTC element 157, thus has the self-temperature control function for maintaining a preset temperature. The electrode interconnects 158a, 158b of the PTC heater 153 are connected to the power supply unit 27. The controller 25 controls the operation of the PTC heater 153 via the power supply unit 27. When desired to maintain the electrophoresis section 115 at a preset temperature with the use of the PTC heater 153, the controller 25 instructs the power supply unit 27 to supply power to the PTC heater 153. Since the PTC heater 153 has the self-temperature control function, the electrophoresis section 115 of the microchip 100 may be maintained at the preset temperature via the heat conductive plate 151.

The configuration of the PTC heater 153 will now be explained.

The PTC element 157 and the electrode interconnects 158a, 158b are arranged on a surface of the resin member 156 which is in contact with the heat conductive plate 151. More specifically, the anode interconnect 158a, the positive voltage is applied to, and the cathode interconnect 158b, the grounding voltage is applied to, are arrayed in the first direction (longitudinal direction) along which the capillaries 116 extend inside of the microchip 100. The electrode interconnects are alternately arrayed on the resin member.

Figure 12:
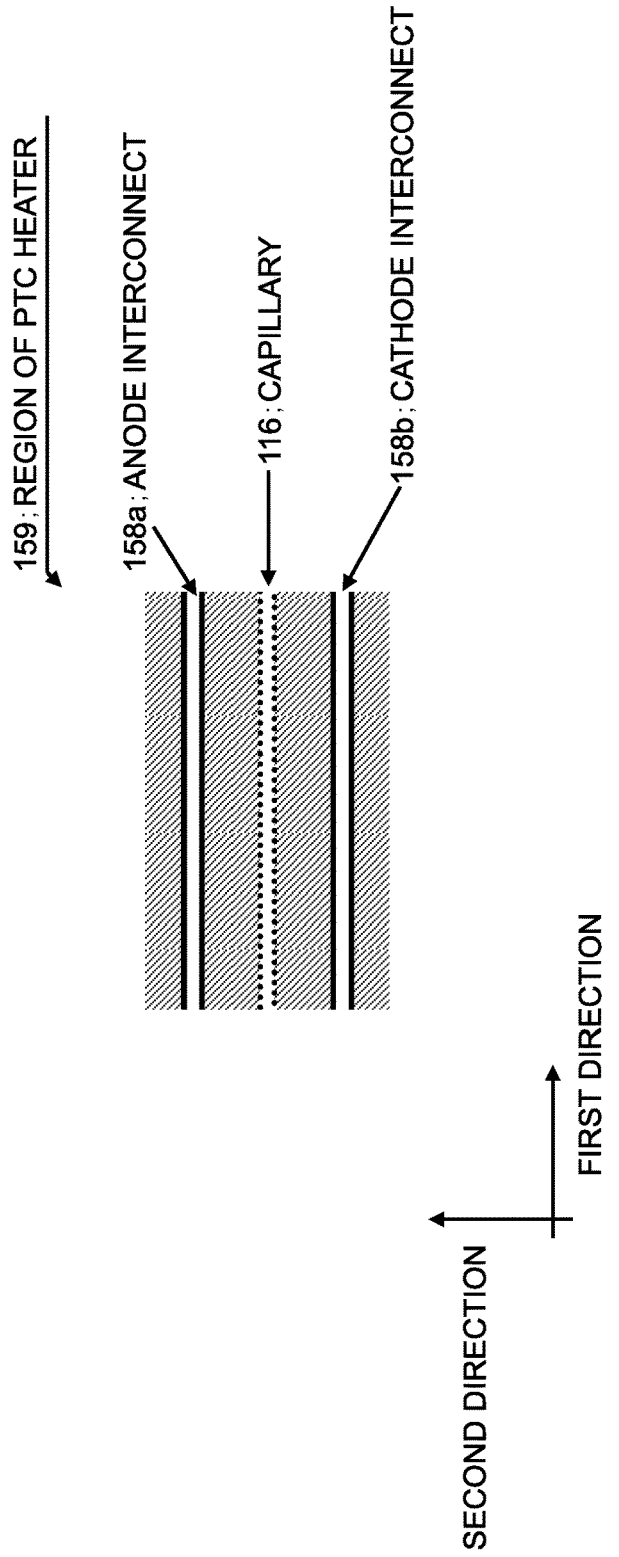
FIG. 12 shows positional relationship between electrode interconnects 158*a*, 158*b* of the PTC heater 153 and a capillary 116 in the microchip 100.

FIG. 12 illustrates the position relationship between the electrode interconnects 158a, 158b of the PTC heater 153 and the capillaries 116 inside of the microchip 100. FIG. 12 shows a region 159 of FIG. 11 in an enlarged scale. In FIG. 12, the capillaries 116 are shown with dotted lines. By referring to FIG. 12, it is seen that the anode interconnect 158a and the cathode interconnect 158b are so arrayed that the capillary 116 is disposed on a middle part between these anode and cathode interconnects. By arranging the anode interconnect 158a and the cathode interconnect 158b on both sides of the capillary 116 in this manner, the temperature at the capillary 116, disposed at a higher height, may be made even. The PTC element 157 has the self-temperature control function, as discussed above. Moreover, since the PTC element 157 is arranged on entire region between the electrode interconnects 158a, 158b disposed on both sides of the capillary 116, the temperature on the region may be regarded to be substantially the same. The reason is that, if temperature of the region surrounding the capillary 116 is the same, the heat supplied via the heat conductive plate 151 to the capillary 116 may be regarded to be the same. That is, it is possible to cancel unevenness in the temperature of the capillary 116 in the first direction.

The heat conductive plate 151 and the PTC heater 153 are provided with the measurement hole 152. In this case, heat diffusion takes place around the measurement hole 152. Thus, if a nichrome wire is used, for example, as a heat source, instead of using the PTC heater 153 as the heat source, there is raised a problem that the temperature around the measurement hole 152 becomes lower than that in other sites. However, if the PTC heater 153 is used as the heat source, the self-temperature control function of the PTC element 157 comes into play, such that, even if the temperature around the measurement hole 152 is lowered owing to the very presence of the measurement hole, such temperature lowering may be compensated. That is, it is possible to render the temperature of the region around the measurement hole 152 and that in the other regions substantially equal to each other to remove the risk of temperature unevenness in the capillaries 116.

Figure 13:
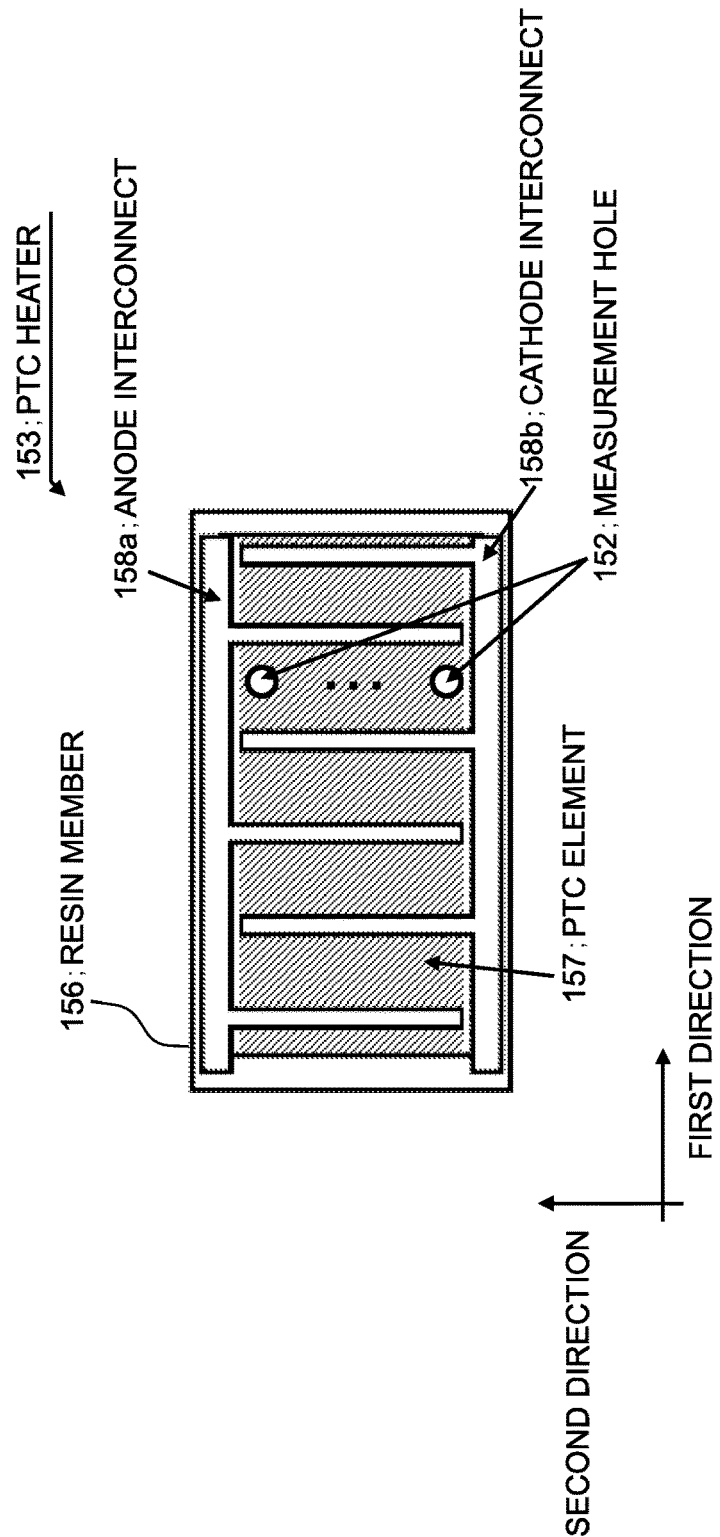
FIG. 13 is an exemplary plan view showing the PTC heater 153.

By the way, the manner of arraying the electrode interconnects 158a, 158b is not limited to that shown in FIG. 11. For example, the pair electrode interconnects 158a, 158b may be arranged in the second direction (transverse direction), as shown in FIG. 13. Or the pair electrode interconnects 158a, 158b may be arranged on both ends of the resin member 156, as shown in FIG. 14, with the electrode interconnects 158a, 158b not being arranged in the center portion of the resin member 156.

Figure 14:
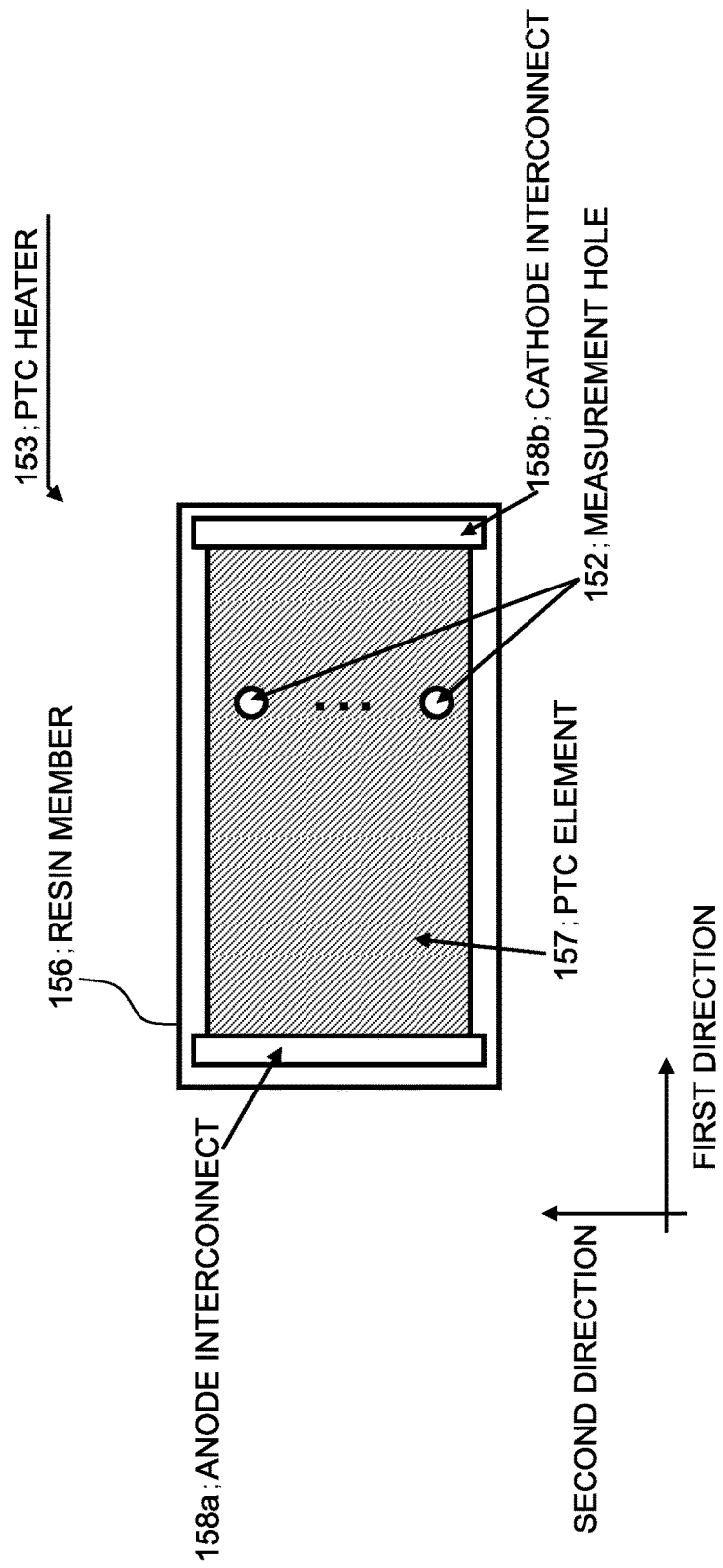
FIG. 14 is another exemplary plan view of the PTC heater 153.

In light of the purpose of providing an even temperature at the capillaries, the arrangement of FIG. 11 is not appreciably different from that of FIG. 14. However, in the arrangement shown in FIG. 14, it is necessary to apply a voltage higher than that shown in FIG. 11 to the anode interconnect 158a. In the arrangement shown in FIG. 11, in which the region where the PTC element 157 is disposed is separated with the electrode interconnects 158a, 158b, it is possible to suppress the voltage applied to the anode interconnect 158a. Due to difference in the manner of laying out of the electrode interconnects 158a, 158b, the voltage applied to the PTC heater 153 differs in the two arrangements.

The arrangement shown in FIG. 13 also differs from that shown in FIG. 11 in that, when the PTC heater 153 is viewed from above, the capillary 116 crosses the electrode interconnects 158a, 158b. Since the PTC element 157 is not provided in regions of crossing of the capillary 116 and the electrode interconnects 158a, 158b, heat is not supplied to the regions. Hence, temperature unevenness is generated between these regions and neighboring regions, thus leading to a possibility that the temperature of the capillaries 116 may not be made even. However, in the arrangement of FIG. 11, it is necessary to design the shape of the microchip 100 as well as the PTC heater 153 so that the capillaries 116 will not be overlapped with the electrode interconnects 158a, 158b, that is, so that the capillaries 116 will be disposed intermediate between the electrode interconnects 158a, 158b. On the other hand, with the arrangement shown in FIG. 13, it is not strictly necessary to pay attention in designing the shape of the microchip 100 or the PTC heater 153. Moreover, if, in the arrangement shown in FIG. 13, the electrode interconnects 158a, 158b extending in the second direction are reduced in width, the adverse effect on the temperature distribution of the capillaries 116 may be thought to be negligibly small. Thus, the manner of arranging the PTC element 157 and the manner or arraying the electrode interconnects 158a, 158b have merits and demerits. In light of the above, the manner of arraying the PTC element 157 and the electrode interconnects 158a, 158b is desirably decided as the power supply unit supplying the power to the PTC element 157, ease in designing and so forth are comprehensibly taken into account.

The operations by a user in carrying out DNA analysis as well as the operation of the DNA analysis apparatus will now be explained.

[Operation by a User]

A user fills the sample solution injection section 101, wash buffer injection section 102, PCR reagent injection section 103, formamide injection section 104 and the electrophoresis polymer injection section 105 with respective solutions and sets the microchip 100 on the DNA analysis apparatus 10. The user then actuates the DNA analysis apparatus 10 to start DNA analysis.

[Sequence of Operations by the DNA Analysis Apparatus]

Figure 15:
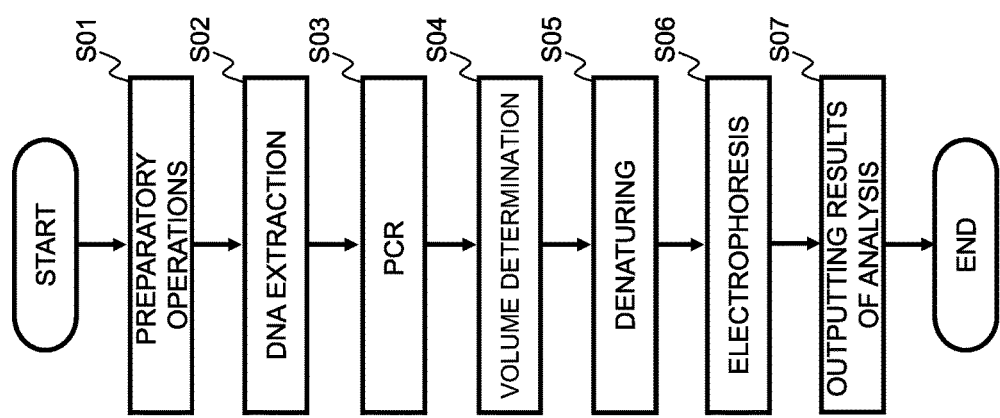
FIG. 15 is a flowchart showing an exemplary operation of the DNA analysis apparatus 10.

FIG. 15 depicts a flowchart showing an example operation of the DNA analysis apparatus 10. When the user has set the microchip 100, and a command to initiate the processing has been admitted, the DNA analysis apparatus 10 carries out preparatory operations (step S01). More specifically, the DNA analysis apparatus 10 maintains the temperature of the denaturing section 114 at a preset value, such as 60° C., with the temperature adjustment unit 13, while maintaining the electrophoresis section 115, in particular the capillaries 116, at another preset value, such as 50° C., with the electrophoresis section 115. The DNA analysis apparatus 10 charges the polymer in the electrophoresis polymer injection section 105 into the capillaries 116.

The DNA analysis apparatus 10 then executes the processing of DNA extraction (step S02). More specifically, the DNA analysis apparatus 10 transfers the sample solution injected into the sample solution injection section 101 to the DNA extraction section 111 to cause the sample DNA to be adsorbed to the magnetic beads (silica) sealed in the DNA extraction section 111. The magnetic beads are rinsed with a wash buffer within the wash buffer injection section 102 to extract the template DNA. The DNA analysis apparatus 10 then transfers the PCR reagent injected into the PCR reagent injection section 103 to the DNA extraction section 111 to elute the sample DNA.

The DNA analysis apparatus 10 then carries out PCR (step S03). Specifically, the DNA analysis apparatus 10 transfers the PCR reagent containing the template DNA from the DNA extraction section 111 to a plurality of PCR sections 112, and performs temperature control of the PCR sections 112, as programmed, via the heat conductive material 131 of the temperature adjustment unit 13.

After accomplishment of the PCR, the DNA analysis apparatus 10 executes volume determination (step S04). Specifically, the DNA analysis apparatus 10 transfers the amplicon containing PCR reagent, referred to as a reaction sample, from the PCR section 112 to the volume determination section 113 until the volume determination section 113 is filled up, then discharging the residual PCR reagent via the drainage port 106.

The DNA analysis apparatus 10 then executes the processing of denaturing (step S05). Specifically, the DNA analysis apparatus 10 transfers formamide injected into the formamide injection section 104 to the denaturing section 114 via the PCR section 112 and the volume determination section 113. Thereby, the reaction sample and formamide are transferred to the denaturing section 114 while being mixed together. The DNA analysis apparatus 10 executes the denaturing processing as the reaction sample is maintained in the volume determination section 113 for a preset reaction time.

The DNA analysis apparatus 10 then executes the processing of electrophoresis (step S06). Specifically, the DNA analysis apparatus 10 transfers the reaction sample from the denaturing section 114 to the electrophoresis section 115 to inject the reaction sample into each capillary 116. The DNA analysis apparatus 10 initiates peak detection by the light receiving unit 155 of the electrophoresis unit, then applying a dc voltage to the capillaries 116 to carry out the processing of electrophoresis.

Finally, the DNA analysis apparatus 10 analyzes DNA length, using the DNA analysis unit 28, and outputs the result of analysis (step S07).

As described above, the DNA analysis apparatus 10 of the present embodiment executes electrophoresis after denaturation processing, thus having an improved analysis precision. That is, since the amplicon comprises a repeat sequence, there is possible occurrence of a bridge structure (FIG. 1 (b)), or a bulge loop structure (FIG. 1 (c)) if the amplicon is of double-strand. In addition, even if the amplicon is of single-strand, there is possible occurrence of a hairpin structure (FIG. 1 (d)). These structures have different migration speeds from straight single-strand amplicon, resulting in generation of a ghost band(s). However, in the first embodiment, denaturation processing is executed, thus such generation of the ghost band is prevented, resulting in improvement in analysis precision.

In addition, in the DNA analysis apparatus 10, the PTC heater 153 is used for controlling temperature, resulting in that temperature unevenness on the heat conducting plate 151 contacting to the PTC heater 135 may be suppressed. There is a risk of generation of so-called smiling, a phenomenon that DNA migrates at low speed if ambient temperature of the capillary is low and that DNA migrates at high speed if ambient temperature of the capillary is high. In such case, generation of smiling leads detection of offset peaks due to the different migration speeds, even under a condition where the peaks of sample and size marker are consistent. To the contrary, if ambient temperature of the capillary is substantially even, the generation of smiling is suppressed, and the offset in peaks due to different migration speed is eliminated, resulting in improvement in analysis precision.

[Modifications]

The above represents merely a preferred mode which may be modified in a number of ways. For example, the conditions for denaturing, such as temperatures, processing time, reagents or the volume of the solutions, may arbitrarily be modified. That is, a diversity of reaction conditions may be applied for denaturing the DNA. For example, the denaturing section 114 mixes the amplicon containing PCR reagent with a keeping reagent (formamide) at a mixing ratio of 1:2 to 1:9. A search conducted by the present inventors has revealed that sufficient results of the processing of denaturing may be obtained in case the mixing ratio of the reaction sample to formamide is 1:9 (1μl to 9μl) and the temperature is 60° C.

The temperature of the processing of denaturing is not limited to 60° C. such that a temperature at which the amplicon as a double strand DNA is denatured to a single strand DNA is sufficient. That is, the temperature of the processing of denaturing is approximately 50 to 98° C. depending on the sequence of the amplicon (Tm value) as well as the formamide/reaction sample mixing ratio.

Although the time of the processing of denaturing is, for example, at least 30 sec, such time which is as long as that tolerable for the user is desirable.

The DNA denaturing agent is not limited to formamide, such that urea, for example, may be used.

The volume of the reaction sample, to be measured by determination process, i.e. the capacity of the volume determination section 113, is preferably as small as possible, provided that it is not so small as to adversely affect peak detection. That is, the greater mixing ratio of formamide to the reaction sample is applied, the higher efficiency of the denaturing would be provided, whereas the peak detected becomes smaller, thus modification should be made, if required. It has been confirmed that, with a sufficiently high denaturing temperature, sufficient results of denaturing may be obtained even if the mixing ratio of the reaction sample and formamide is 1:2.

In a manual operation, conducted at a laboratory, such a protocol is known in which an amplicon is purified by ethanol precipitation and dissolved in formamide. A sample containing the amplicon is heated to 98° C. and then rapidly cooled to 0° C. This protocol may be referred to in order to provide an amplicon purifying configuration on the DNA analysis apparatus 10 and on the microchip 100. The amplicon, may, for example, be purified using the process of DNA extraction with the above mentioned magnetic beads. It is also possible for the DNA analysis apparatus 10 to perform temperature control so that the denaturing section 114 will be kept at 98° C. and then rapidly cooled to 0° C. It is also possible for the temperature adjustment unit 14 by itself to manage temperature control. Or, a hollow structure as well as a temperature adjustment unit, configured for heating to 98° C., and a hollow structure as well as a temperature adjustment unit, configured for cooling to 0° C., may be provided independently of each other.

It is also possible for the PCR section 112 to execute the denaturing processing without carrying out the volume determination processing. For example, it is possible to add formamide after accomplishment of PCR and to manage temperature control for maintaining the PCR section 112 at 98° C. and subsequently cooling it to 0° C. In such case, it is feared that, since the ratio of mixing the reaction sample to formamide becomes larger, the denaturing efficiency may tend to be lowered. However, it may be contemplated that, by adding the amplicon purifying process, it is possible to prevent the denaturing efficiency from being lowered. In such case, since the temperature adjustment unit 14, volume determination section 113 and the denaturing section 114 are not required, it may be expected to reduce the size of the DNA analysis apparatus 10.

On the other hand, it has been ascertained that, in case the mixing of the formamide and the reaction sample is insufficient, the efficiency of the denaturing processing is lowered. It is thus possible to add the processing of mixing of formamide and the reaction sample, such as shuffling the mixture solution between the PCR section 112 and the denaturing section 114.

The above described exemplary embodiment is directed to an electrophoresis apparatus used for DNA analysis. It is however not intended to limit the use of the electrophoresis apparatus to DNA analysis. For example, the subject of analysis may be ions or low molecular compounds. Additionally, DNA analysis is not limited to identification of individuals for criminal investigation and may also be used for detection of gene deletion.

Part or all of the above described exemplary embodiments may non-restrictively be expressed as following modes, but not limited thereto.

[Mode 1]
Same as the microchip according to the above mentioned first aspect.

[Mode 2]
The microchip according to mode 1, wherein. the amplicon amplified by the PCR section is allowed to flow into the denaturing section along with a keeping reagent.

[Mode 3]
The microchip according to mode 1 or 2, wherein the denaturing section is maintained at a preset temperature.

[Mode 4]
The microchip according to any one of modes 1 to 3, further comprising a volume determination section having a capacity smaller than that of the PCR section.

[Mode 5]
The microchip according to any one of modes 1 to 4, wherein the PCR reagent comprising the amplicon and the keeping agent are mixed at a mixing ratio of about 1:2 to 1:9 in the denaturing section.

[Mode 6]
The microchip according to any one of modes 1 to 5, wherein the keeping agent is formamide.

[Mode 7]
Same as the DNA analysis method according to the above mentioned second aspect.

[Mode 8]
Same as the DNA analysis system according to the above mentioned third aspect.

The disclosures of the above mentioned non-Patent Literatures and so forth are to be incorporated herein by reference. The exemplary embodiments or Examples may be modified or adjusted within the concept of the entire disclosures of the present invention, inclusive of claims, based on the fundamental technical concept of the invention. A series of combinations or selections of elements herein disclosed (elements of claims, Examples and drawings) may be made within the context of the claims of the present invention. That is, the present invention may include a wide variety of changes or corrections that may occur to those skilled in the art in accordance with the total disclosures inclusive of the claims and the drawings as well as the technical concept of the invention. In particular, it should be understood that any optional numerical figures or sub-ranges contained in the ranges of numerical values set out herein ought to be construed to be specifically stated even in the absence of explicit statements.

REFERENCE SIGNS LIST

10 DNA analysis apparatus
11 base member
12 table
13, 14 temperature adjustment units
15 electrophoresis unit
16 lid
17 hinge
18a, 18b pins
19a, 19b pin holes
20 set of electrodes
21 pressurizing hole
22 tubes
23 solenoid valve
24 pressure accumulator
25 controller
26 electromagnet
27 power supply unit
28 DNA analysis unit
100 microchip
101 sample solution injection section
102 wash buffer injection section
103 PCR reagent injection section
104 formamide injection section
105 electrophoresis polymer injection section
106 drainage port
111 DNA extraction section
112 PCR section
113 volume determination section 114 denaturing section
115 electrophoresis section
116 capillarie
117 electrode chamber
131, 131a heat conductive material
132, 132a temperature sensors
133 Peltier element
134 heat dissipation plate
151 heat conductive plate
152 measurement hole
153 PTC heater
154 laser output unit
155 light receiving unit
156 resin member
157 PTC element
158a anode interconnect
158b cathode interconnect
159 region of PTC heater
200 flow path

The invention claimed is:

1. A microchip, comprising:
a PCR section in which a desired region in DNA is amplified;
a volume determination section which is arranged downstream of the PCR section and has a capacity smaller than that of the PCR section,
a denaturing section which is arranged downstream of the volume determination section and in which amplicon whose volume is determined in the volume determination section is denatured from double-strand DNA into single-strand DNA; and
an electrophoresis section in which the amplicon denatured in the denaturing section is separated based on the length of sequence.

2. The microchip according to claim 1, wherein
the microchip further comprises a formamide injection section storing a keeping reagent that keeps DNA in a single-strand state, and
the denaturing section mixes the amplicon whose volume is determined in the volume determination section with the keeping reagent.

3. The microchip according to claim 2, further comprising a temperature controller configured to maintain the mixture of the amplicon and the keeping reagent in the denaturing section at a preset temperature.

4. The microchip according to claim 2, wherein the keeping reagent is formamide.

5. A DNA analysis system, comprising:
a microchip comprising:
a PCR section in which a desired region in a template DNA is amplified;
a volume determination section which is arranged on downstream of the PCR section and has a capacity smaller than that of the PCR section;
a denaturing section which is arranged on downstream of the volume determination section and in which amplicon whose volume is determined in the volume determination section is denatured from double-strand DNA into single-strand DNA; and
an electrophoresis section in which the amplicon denatured in the denaturing section is separated based on the length of sequence; and
a DNA analysis apparatus for executing DNA analysis by controlling PCR in the PCR section, denaturation in the denaturing section, and electrophoresis in the electrophoresis section.

* * * * *